United States Patent [19]

Ueno

[11] Patent Number: 5,504,543
[45] Date of Patent: Apr. 2, 1996

[54] OPHTHALMIC PHOTOGRAPHING APPARATUS HAVING CONTROL MEANS FOR STOPPING THE OPERATION AND FIXING THE IN-FOCUS STATE

[75] Inventor: Yasunori Ueno, Kawasaki, Japan

[73] Assignee: Nikon Corporation, Tokyo, Japan

[21] Appl. No.: 503,414

[22] Filed: Jul. 17, 1995

[30] Foreign Application Priority Data

Jul. 25, 1994 [JP] Japan ................................ 6-192790

[51] Int. Cl.6 .............................. A61B 3/14; G03B 29/00
[52] U.S. Cl. .............................................. 351/206; 354/62
[58] Field of Search ................................... 351/205, 206, 351/211, 221, 216; 354/62

[56] References Cited

U.S. PATENT DOCUMENTS 4,452,517  6/1984  Kohayakawa ........................... 351/206

FOREIGN PATENT DOCUMENTS 61-122837  6/1986  Japan .
62-41637  2/1987  Japan .

Primary Examiner—William L. Sikes
Assistant Examiner—Huy Mai
Attorney, Agent, or Firm—Shapiro and Shapiro

[57] ABSTRACT

The ophthalmic photographing apparatus of the present invention is provided with an illuminating optical system for applying illuminating light to the fundus oculi of an eye to be examined, a photographing and observation system for receiving reflected light from the fundus oculi of the eye to be examined and photographing and observing the fundus oculi of the eye to be examined, an index projecting optical system for projecting an index onto the fundus oculi of the eye to be examined, a focus detection optical system for receiving the index of the fundus oculi of the eye to be examined and detecting focus information, a focusing operation system for moving a focusing relay lens along the optical axis thereof on the basis of the focus information to thereby focus the photographing and observation system on the fundus oculi of the eye to be examined, and control means for temporarily positioning and holding the focusing relay lens at a point of time whereat an in-focus state has been detected on the basis of the focus information.

4 Claims, 4 Drawing Sheets

5,504,543

OPHTHALMIC PHOTOGRAPHING APPARATUS HAVING CONTROL MEANS FOR STOPPING THE OPERATION AND FIXING THE IN-FOCUS STATE

BACKGROUND OF THE INVENTION

1. Field of the Invention

This invention relates to an ophthalmic photographing apparatus, and more particularly to the focus detection of a retinal camera.

2. Related Background Art

Generally in an apparatus for observing or measuring an eye, it is very difficult to focus the apparatus on the fundus oculi, due to the deficiency of the quantity of light and the badness of contrast attributable to the low reflectance of the fundus oculi. Particularly, when observing the image of the fundus oculi by the use of fluorescence or infrared fluorescence, the image of the fundus oculi being observed lacks a feeling of color (the image becomes black and white when the observation system is a TV monitor) and therefore it is difficult for contrast to be given to the image and it is more difficult to focus the apparatus (a photographing optical system and an observation optical system) on the fundus oculi.

As described above, in an ophthalmic photographing apparatus such as a conventional retinal camera, there has been the inconvenience that it is difficult to focus the apparatus on the fundus oculi.

SUMMARY OF THE INVENTION

The present invention has been made in view of the above-noted problem and the object thereof is to provide an ophthalmic photographing apparatus of which the focus detection is easy and which is easy to use.

In order to solve the above-noted problem, the present invention provides an ophthalmic photographing apparatus characterized by the provision of an illuminating optical system for applying illuminating light to the fundus oculi of an eye to be examined, a photographing and observation system for receiving reflected light from said fundus oculi of the eye to be examined and photographing and observing said fundus oculi of the eye to be examined, an index projecting optical system for projecting an index onto said fundus oculi of the eye to be examined, a focus detection optical system for receiving said index of said fundus oculi of the eye to be examined and detecting focus information, a focusing operation system for moving a focusing relay lens along the optical axis thereof on the basis of said focus information to thereby focus said photographing and observation system on the fundus oculic of the eye to be examined, and control means for temporarily positioning and holding said focusing relay lens at a point of time whereat an in-focus state has been detected on the basis of said focus information.

According to a preferred embodiment of the present invention, the ophthalmic photographing apparatus is further provided with selecting means for selecting whether said focusing relay lens is to be temporarily positioned and held through said control means, and focus information observation means for observing said detected focus information.

The ophthalmic photographing apparatus of the present invention is provided with the control means for temporarily positioning and holding said focusing relay lens at a point of time whereat the in-focus state has been detected on the basis of the focus information. Further, by a light source for the index being turned off, only a fundus image of good quality in focus can be observed on an observation image plane, e.g. a TV monitor.

Also, when it is desired to photograph a region of which the focus detection is difficult, the focusing relay lens is positioned and held at an in-focus position by another region of which the focus detection is easy on the basis of the focus information. If thereafter, photographing is effected with the apparatus turned toward the region of which the focus detection is difficult, photographing in focus even on the region of which the focus detection is difficult can be effected.

DESCRIPTION OF THE PREFERRED EMBODIMENT

An embodiment of the present invention will hereinafter be described with reference to the accompanying drawings.

Figure 1:
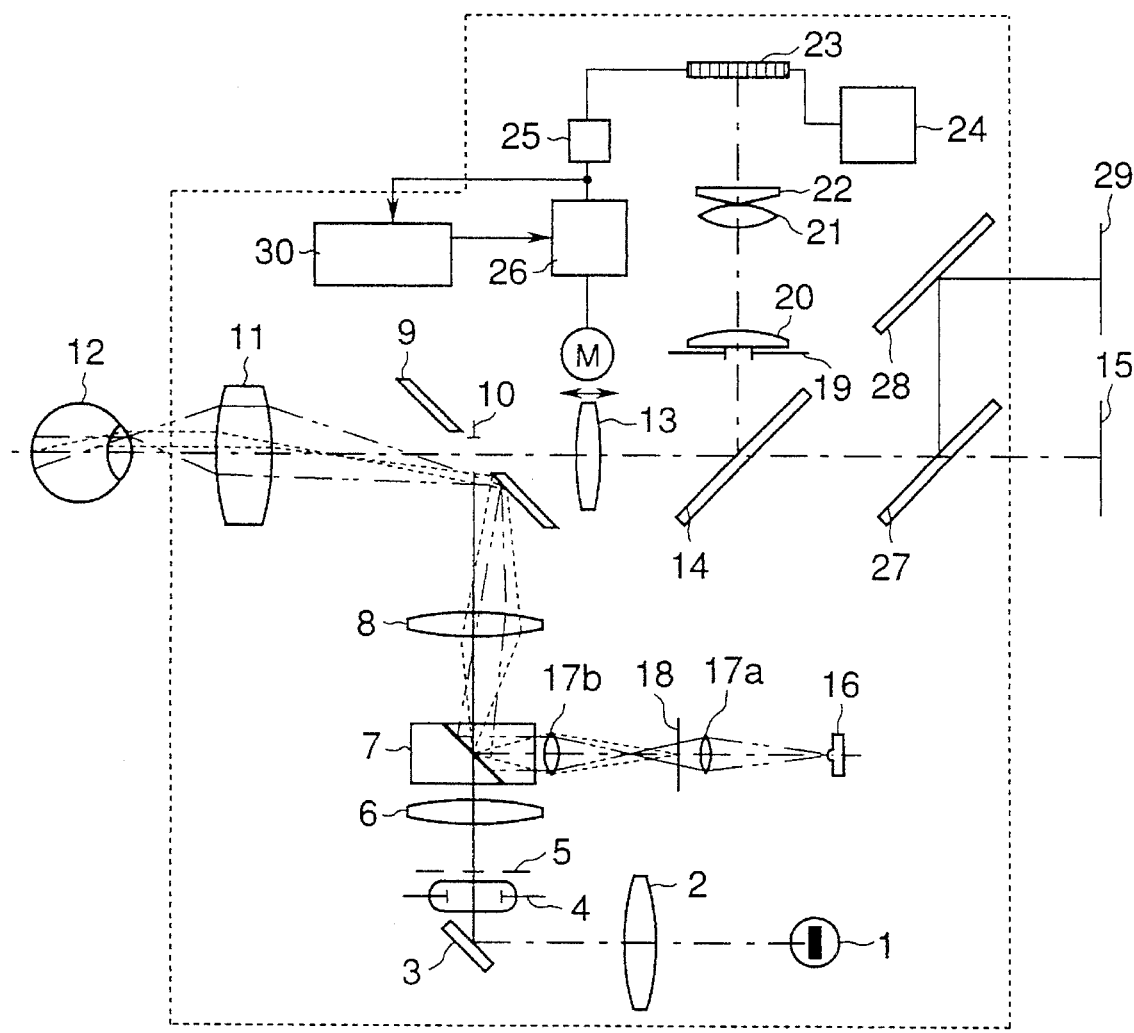
FIG. 1 schematically shows the construction of an ophthalmic photographing apparatus according to an embodiment of the present invention.

FIG. 1 schematically shows the construction of an ophthalmic photographing apparatus according to an embodiment of the present invention. The ophthalmic photographing apparatus shown is a retinal camera comprised of an illuminating optical system for illuminating the fundus oculi of an eye to be examined, an index projecting optical system for projecting an index onto the fundus oculi of the eye to be examined, a focus detection optical system for receiving light from the index projected onto the fundus of the eye to be examined and effecting the detection of the focusing on the fundus oculi of the eye to be examined, an observation optical system for observing the state of the fundus oculi of the eye to be examined, and a photographing optical system for photographing the state of the fundus oculi of the eye to be examined.

In FIG. 1, the illuminating optical system is provided with an illuminating light source 1 for observation. Light emitted from the illuminating light source 1 for observation enters a reflecting mirror 3 through a relay lens 2 for the light source, and is reflected upwardly as viewed in FIG. 1. The light reflected by the reflecting mirror 3 enters a relay lens 6 for a ring slit through a ring slit 5.

Figure 3:
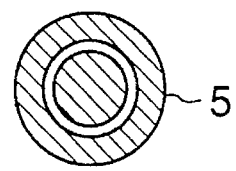
FIG. 3 shows the opening portion of the ring slit of FIG. 1.

At a position conjugate with the illuminating light source 1 by the relay lens 2 for the light source, there is disposed a strobe tube 4 as an illuminating light source for photographing. Also, the ring slit 5 has a circular slit opening portion centering around the optical axis, as shown in FIG. 3.

The light passed through the, relay lens 6 for the ring slit (the light from the illuminating light source 1 for observation and the light from the strobe tube 4) is transmitted through a dichroic prism 7 and enters an apertured mirror 9 through another relay lens 8 for the ring slit. The light reflected leftwardly as viewed in FIG. 1 by the apertured mirror 9 illuminates the fundus oculi of an eye 12 to be examined through an objective lens 11. As is well known, the working distance between the apparatus of the present embodiment and the eye 12 to be examined is adjusted by the two relay lenses 6 and 8 for the ring slit and the objective lens 11 so that the ring slit 5 may be substantially conjugate with the cornea of the eye 12 to be examined.

Figure 4:
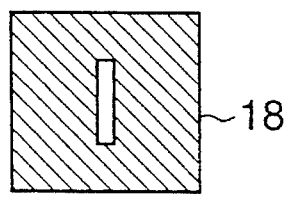
FIG. 4 shows a slit formed in the index plate of FIG. 1.

On the other hand, the index projecting optical system is provided with a light source (point light source) 16 for index projection comprising, for example, an infrared light emitting diode. Infrared light. (indicated by dots-and-dash line in FIG. 1) emitted from the light source 16 for index projection illuminates an index plate 18 through a relay lens 17a for the index projecting system. As shown in FIG. 4, the index plate 18 is formed with a slit having its lengthwise direction parallel to the plane of the drawing sheet.

The light transmitted through the slit of the index plate 18 is once imaged, whereafter it enters the dichroic prism 7 through a relay lens 17b for the index projecting system. The light having entered the dichroic prism 7 is reflected upwardly as viewed in FIG. 1 by the reflecting surface thereof, and is again imaged near the apertured mirror 9 through the relay lens 8 for the ring slit. The light reflected leftwardly as viewed in FIG. 1 by the apertured mirror 9 is imaged near the pupil of the eye 12 to be examined through the objective lens 11 and illuminates the fundus oculi of the eye 12 to be examined.

In the above-described illuminating optical system and index projecting optical system, the dichroic prism 7 has the characteristic of reflecting infrared light and transmitting visible light therethrough. Accordingly, the visible light from the light source 1 for observation and from the strobe tube 4 (the illuminating light source for photographing) is transmitted through the dichroic prism 7, while the infrared light from the light source 1 for observation and from the strobe tube 4 is reflected and goes out of the illuminating optical system.

On the other hand, as indicated by broken lines in FIG. 1, the slit of the index plate 18 is imaged near the dichroic prism 7 by the relay lens 17b for the index projecting system, and thereafter is reflected upwardly as viewed in FIG. 1. The reflected light is imaged at the rear focus position of the objective lens 11 through the relay lens 8 and the apertured mirror 9. Accordingly, the transmitted light of slit passed through the objective lens 11 becomes substantially parallel light and enters the eye 12 to be examined. As a result, if the eye 12 to be examined is an emmetropia, the slit of the index plate 18 is imaged on the fundus oculi. In other words, the slit image (index image) of the index plate 18 is defocused in conformity with the diopter of the eye 12 to be examined.

Figure 2:
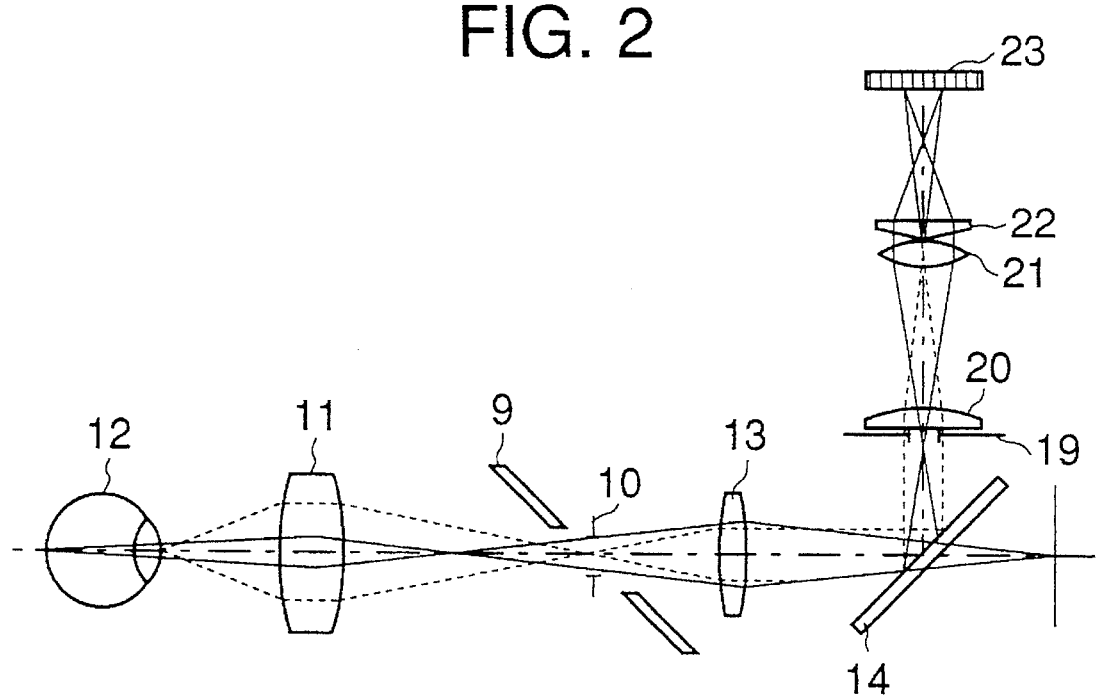
FIG. 2 shows the construction of the focus detection optical system of the ophthalmic photographing apparatus shown in FIG. 1.

FIG. 2 shows the construction of only the focus detection optical system of the ophthalmic photographing apparatus shown in FIG. 1.

As indicated by solid lines in FIG. 2, the slit image of the index plate 18 projected onto the fundus oculi of the eye 12 to be examined becomes a secondary light source and is once imaged through the objective lens 11, whereafter it passes through the central opening portion of the apertured mirror 9 and an aperture stop 10 and enters a focusing relay lens 13. The infrared light passed through the focusing relay lens 13 enters a dichroic mirror 14 having the characteristic of reflecting infrared light and transmitting visible light therethrough. The light reflected upwardly as viewed in FIG. 2 by the dichroic mirror 14 is once imaged near a field stop 19, whereafter it enters a field lens 20. The light passed through the field lens 20 enters an array sensor 23 through a re-imaging lens 21 and a pupil dividing prism 22.

On the other hand, the reflected light from the fundus oculi of the eye 12 to be examined illuminated by the visible light from the light source 1 for observation and from the strobe tube 4 (the illuminating light source for photographing) is transmitted through the dichroic mirror 14 and is imaged on a photographing image plane 15. A quick return mirror 27 is disposed between the dichroic mirror 14 and the photographing image plane 15. Accordingly, the light transmitted through the dichroic mirror 14 is reflected upwardly as viewed in FIG. 2 by the quick return mirror 27, whereafter it is imaged on an image pickup surface 29 for a TV monitor or the like via a mirror 28, and this image is displayed on the TV monitor or the like and observed by an examiner. The TV monitor or the like is not shown. The quick return mirror 27, the mirror 28 and the image pickup surface 29 are not shown in FIG. 2.

Thus, the fundus oculi of the eye 12 to be examined can be observed on the TV monitor or the like on which is displayed the image of the image pickup surface 29 for the TV monitor or the like, and the fundus oculi of the eye 12 to be examined can be photographed or the photographing image plane 15.

Since as described above, the dichroic mirror 14 has the characteristic of reflecting infrared light and transmitting visible light therethrough, only the light transmitted through the index plate 18 illuminated by the light source 16 for index projection arrives at the array sensor 23. As a result, the index image (in the present embodiment, the slit image) formed on the array sensor 23 becomes an image of good contrast.

The field stop 19 is disposed at a position conjugate with the array sensor 23 by the re-imaging lens 21. Also, the array sensor 23 is conjugate with the photographing image plane 15 and the image pickup surface 29.

Thus, the slit image (the index image) from the fundus oculi of the eye 12 to be examined is formed near the array sensor 23 by the re-imaging lens 21. At that time, the beam of light passed through the pupil dividing prism 22 is divided into two beams of light by the pupil dividing prism 22. The divided beams of light, as shown in FIG. 2, are imaged on different areas (cells) on the array sensor 23.

Figure 5:
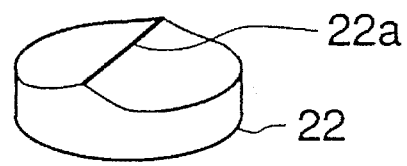
FIG. 5 is a perspective view showing the construction of the pupil dividing prism of FIG. 1.

A perspective view of the pupil dividing prism 22 is shown in FIG. 5. In FIGS. 1 and 2, the ridgeline 22a of the pupil dividing prism 22 is depicted perpendicularly to the plane of the drawing sheet, but this is for the convenience of expression, but actually the pupil dividing prism 22 is disposed in such a manner that the ridgeline 22a of the pupil dividing prism 22 is rotated by 90° around the optical axis and becomes parallel to the plane of the drawing sheet. As a result, in conformity with the direction of the ridgeline of the pupil dividing prism 22, the direction of arrangement of the cells of the array sensor 23 is also a direction perpendicular to the plane of the drawing sheet. It is preferable to make the lengthwise direction of the slit image and the direction of the ridgeline of the pupil dividing prism 22 coincident with each other in this manner.

On the other hand, as indicated by broken line in FIG. 2, the ridgeline of the pupil dividing prism 22 is made substantially conjugate with the aperture stop 10 by the focusing relay lens 13 and the field lens 20. This aperture stop 10 corresponds to the exit pupil of the focus detection optical system and therefore, the images on the array sensor 23 are ones formed by the beams of light from the two different portions of the pupil of this optical system. The two images on the array sensor 23 thus obtained, as is well known, cause lateral diviation relative to each other in conformity with the so-called front focus state and rear focus state. Accordingly, by measuring the spacing between the two images on the array sensor 23, it is possible to effect the detection of the focus state.

Figure 6:
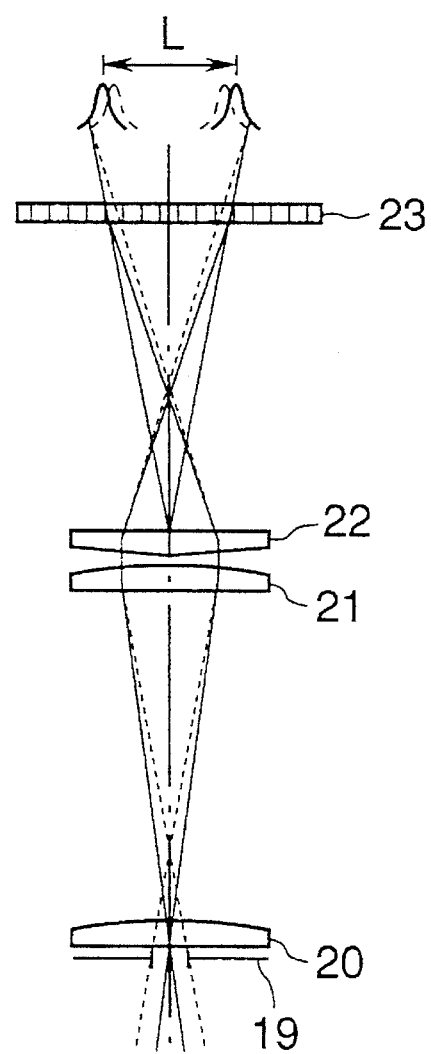
FIG. 6 illustrates the principle of focus detection.

That is, assuming that as indicated by solid line in FIG. 6, the spacing between the two images on the array sensor 23 is L under an in-focus state, the inter-image spacing becomes smaller than the reference spacing L as indicated by broken line in FIG. 6 under the so-called rear focus state in which the position of focus lies rearwardly (above as viewed in FIG. 6) of the field stop 19. On the other hand, under the so-called front focus state in which the position of focus lies forwardly (below as viewed in FIG. 6) of the field stop 19, although not shown, the inter-image spacing becomes greater than the reference spacing L.

Thus, the spacing between the two slit images on the array sensor 23 is measured and compared with the reference spacing under the in-focus state, whereby focus information can be obtained.

As shown in FIG. 1, the cells of the array sensor 23 are successively driven on the basis of a signal from driving means 24 and photoelectric conversion signals corresponding to the respective cells are successively outputted from the array sensor 23 to calculating means 25. In the calculating means 25, the spacing between the two slit images is measured on the basis of the photoelectric conversion signals from the array sensor 23, and the measured spacing is compared with the reference spacing under the in-focus state. On the basis of focus information thus obtained by the calculating means 25, a motor M is driven by motor driving means 26 to thereby suitably move the focusing relay lens 13 along the optical axis, whereby the fundus oculi of the eye 12 to be examined can be focused on the array sensor 23 and further, on the photographing image plane 15 and the image pickup surface 29.

When the fundus oculi of the eye to be examined is to be photographed, the light source 16 for the index is of course turned off before the strobe tube 4 emits light.

In the present embodiment, the light source 16 for illuminating the index emits infrared light. The dichroic mirror 14 used in this embodiment is of a type which reflects infrared light and transmits visible light. But it is difficult for present technology to manufacture a mirror which perfectly reflects infrared light. So a portion of infrared light may possibly be transmitted through the dichroic mirror. Therefore, some of the infrared light from the light source 16 which is transmitted through the dichroic mirror 14 arrives at the photographing image plane 15 and the image pickup surface 29, and the index image is displayed on the TV monitor for displaying the image formed or the image pickup surface 29. As a result, on the TV monitor, the image of the fundus oculi to be observed and the index image are superposed one upon the other and the quality of image is remarkably spoiled.

As described above, the motor driving means 26 drives the motor M on the basis of the focus information obtained by the focus detection optical system to thereby move the focusing relay lens 13 along the optical axis, thus effecting focusing.

The apparatus of the present embodiment is provided with control means for receiving the focus information obtained by the calculating means 25, stopping the driving of the motor M through the motor driving means 26 at the point of time of focusing, and temporarily positioning and holding the focus relay lens 13 at an in-focus position. This control means 30 further turns off the light source 16 for the index.

As described above, at the point of time of focusing, the focusing relay lens 13 is temporarily positioned and held at the in-focus position and the light source 16 for the index is turned off, whereby the index image is no longer displayed on the TV monitor for displaying the image of the image pickup surface 29. Accordingly, the image of the fundus oculi alone is observed on the TV monitor. Moreover, the focusing relay lens 13 is positioned and held at the in-focus position and therefore, the image of the fundus oculi of good image quality in focus can be observed on the TV monitor.

The technique of positioning and holding the focusing relay lens 13 at the in-focus position is also useful when photographing any region which is not easy to focus. For example, when it is desired to photograph a region of detachment of the retina on which focus detection is difficult, focus information is detected in another region on which focus detection is easy, and the driving of the motor M is stopped to thereby position and hold the focusing relay lens 13 at the in-focus position. Thereafter, photographing is effected with the retinal camera turned toward the region of detachment of the retina on which focus detection is difficult. Thus, photographing in focus on any region on which focus detection is difficult can be accomplished.

Figure 7:
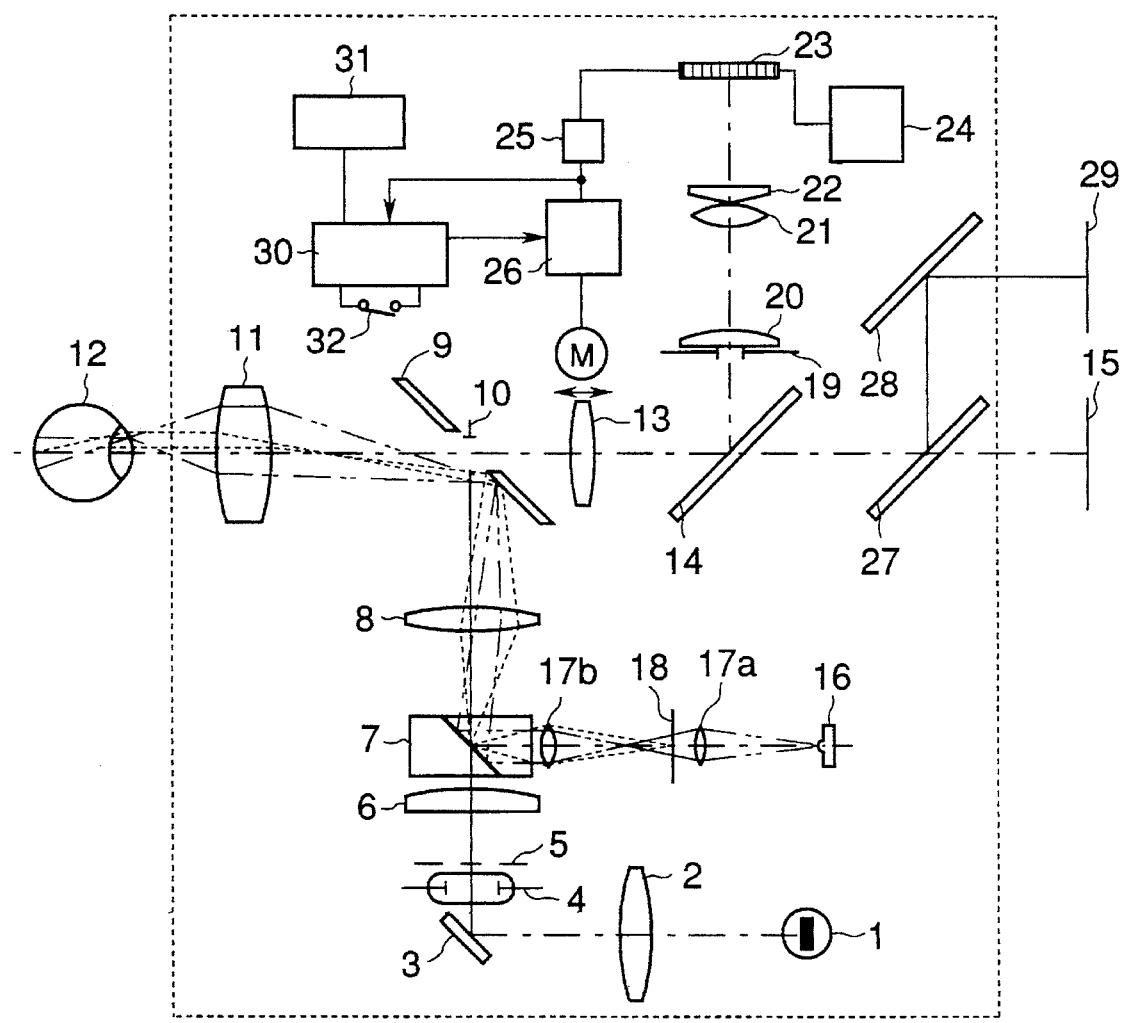
FIG. 7 schematically shows a modification of the apparatus shown in FIG. 1.

It is preferable that the apparatus be further provided with selecting means for selecting whether or not at the point of time of focusing, the focusing relay lens 13 is to be temporarily positioned and held at the in-focus position, and focus information displaying means for displaying the focus information obtained by the calculating means 25. FIG. 7 shows a modification of the apparatus shown in FIG. 1 which is provided with such a construction. In FIG. 7, the same portions as those in FIG. 1 are given the same reference characters and need not be described. The modification shown in FIG. 7 has displaying means. 31 for displaying focus information, and a changeover switch 32 for selecting whether or not the focusing relay lens 13 is to be held at the in-focus position.

As described above, the modification is provided with the selecting means and the focus information displaying means, whereby it can more easily and accurately effect focusing on and photographing of any region on which focus detection is difficult.

While in the above-described embodiment, infrared light is used as the light for illuminating the index, other light such as near infrared light can also be used.

As described above, according to the present invention, there can be realized an ophthalmic photographing apparatus of which the focus detection is easy and which is easy to use.

What is claimed is:

1. An ophthalmic photographing apparatus comprising:

an illuminating optical system for applying illuminating light to the fundus oculi of an eye to be examined;

an observation/photographing system for receiving reflected light from said fundus oculi of the eye to be examined and observing/photographing said fundus oculi of the eye to be examined;

an index projecting optical system for projecting an index onto said fundus oculi of the eye;

a focus detection optical system for receiving light from said index projected onto said fundus oculi of the eye to be examined and detecting information about the in-focus state of said observation/photographing system;

a focusing operation system for moving a focusing relay lens along the optical axis thereof on the basis of said information to thereby focus said observation/photographing system on said fundus oculi of the eye to be examined; and control means for stopping the operation of said focusing operation system when said focus detection optical system detects the focusing on said fundus oculi of the eye to be examined, and fixing the in-focus state of said observation/photographing system.

2. The apparatus of claim 1, wherein said control means stops driving means for driving said focusing relay lens to thereby fix the in-focus state of said observation/photographing system.

3. The apparatus of claim 1, further comprising setting means for selectively setting whether said control means is to perform the operation of fixing the in-focus state of said observation/photographing system, and displaying means for displaying said in-focus state detected by said focus detection optical system.

4. The apparatus of claim 1, wherein said control means is capable of turning off the light source of said index projecting optical system at a point of time whereat said focus detection optical system has detected the in-focus state on the fundus oculi of the eye to be examined.

* * * * *